US006496781B1

(12) United States Patent
Chen et al.

(10) Patent No.: US 6,496,781 B1
(45) Date of Patent: Dec. 17, 2002

(54) MIXTURE CONCENTRATION CONTROL IN MANUFACTURING PROCESSES

(75) Inventors: Qingyuan Chen, Appleton, WI (US); Robert J. Franda, Sherwood, WI (US)

(73) Assignee: Appleton Papers Inc., Appleton, WI (US)

( * ) Notice: Subject to any disclaimer, the term of this patent is extended or adjusted under 35 U.S.C. 154(b) by 0 days.

(21) Appl. No.: 09/893,883

(22) Filed: Jun. 29, 2001

(51) Int. Cl.$^7$ .......................... G01N 31/00; G06F 19/00
(52) U.S. Cl. .......................... 702/25; 702/22; 702/23; 702/24; 702/137; 700/265; 73/53.01
(58) Field of Search .......................... 72/25, 24, 23, 72/22, 137; 700/265, 266, 285; 73/53.01, 19.01

(56) References Cited

U.S. PATENT DOCUMENTS 5,365,435 A * 11/1994 Stephenson ............... 700/265

OTHER PUBLICATIONS

Bergman and Roitto, "On–Line Measurement of Coating Color Quality in Coater Supply System", 1999 Tappi Coating Conference (Toronto, Canada), May, 1999.

\* cited by examiner

Primary Examiner—John S. Hilten
Assistant Examiner—Hien Vo
(74) Attorney, Agent, or Firm—Birch, Stewart, Kolasch & Birch, LLP (57) ABSTRACT

The present invention provides an improvement to the two, inaccurate, traditional approaches relating concentration to density. The first of these assumes that the solute is completely insoluble in the solvent; the second is based on a soluble solute. The present improved relationship is referred to as the CONCENTRATION-DENSITY MODEL. This model allows for a theoretical determination of the concentration-density relationship for a multi-component solid/liquid or liquid/liquid mixture. Included in the Concentration-Density Model is a new concept referred to as ADDITIVE VOLUME COEFFICIENT (AVC). This concept compensates for the fact that the net volume of a mixture does not always equal the sum of the volumes of each component. This improved Concentration-Density Model provides fluid-handling manufacturers with a method for accurately determining a mixture's concentration on-line with the aid of current density measurement instrumentation. By allowing for accurate concentration determination in manufacturing scenarios where such measures were previously impractical, the present invention enables improved control of the manufacturing process.

11 Claims, 3 Drawing Sheets

MIXTURE CONCENTRATION CONTROL IN MANUFACTURING PROCESSES

FIELD OF INVENTION

This invention relates to the determination of the concentration of a multi-component solid/liquid or liquid/liquid mixture. It can be applied to any situation where the density of such a mixture is known or can be determined. This invention provides a means for improving the control of a continuous process which handles such a mixture and is dependent on the mixture's concentration, and can thus assist manufacturers in effectively monitoring and operating their processes. Data generated by this invention can be used to: control a known process fluid to a targeted concentration, for instance in a paper coating process; verify on-line the accuracy of batchwise or continuous ratio blends in the manufacture of such products as food products (ketchup, mayonnaise, syrup), personal care products (skin cream, shampoo), pharmaceutical products, paints, petroleum blends, and the like; and eliminate the excessive empirical work necessary with density monitoring process control systems.

BACKGROUND OF THE INVENTION

The solute content of a solid/liquid or liquid/liquid mixture—commonly expressed as the mixture's concentration—can be determined from the mixture's true density utilizing a relationship that exists between the mixture's concentration and density. This relationship consists of a linear correlation between a mixture's concentration and density, which is unique to each mixture. Stated generally, a unique, linear relationship exists for any solute/solvent mixture (solution or slurry).

Defined hereinbelow is an improvement to the two inaccurate, traditional approaches relating concentration to density. The first, the Non-linear Model, assumes that the solute is completely insoluble in the solvent. The second, the Linear Model, is based on a soluble solute. The present improved relationship is referred to as the CONCENTRATION-DENSITY MODEL. This model allows for a theoretical determination of the concentration-density relationship for a multi-component solid/liquid or liquid/liquid mixture. Included in the Concentration-Density Model is a new concept referred to as ADDITIVE VOLUME COEFFICIENT (AVC). This concept compensates the Non-linear Model for the fact that the net volume of a mixture does not always equal the sum of the volumes of each component.

As described in detail herein, this improved Concentration-Density Model provides fluid-handling manufacturers with a method for accurately determining a mixture's concentration on-line with the aid of current density measurement instrumentation. The Concentration-Density Model of the present invention allows for accurate concentration determination in manufacturing scenarios where such measures were previously impractical. These concentration measurements can then be used to control the manufacturing process.

It is common for a solid/liquid mixture's concentration to be determined in a laboratory by measuring the weight of a sample both before and after evaporating the liquid phase of the mixture. This approach can be very accurate, but must occur off-line which results in a significant time delay between the time of sampling and the time of measurement. This time delay decreases the number of manufacturing applications where this measurement is useful.

Other methods, either off-line or on-line, determine concentration indirectly. A property of a solid/liquid or liquid/liquid mixture (e.g., density, gamma radiation absorption, and so on) is empirically correlated to a mixture's concentration. The mixture's concentration can then be calculated from a measurement of that property (on-line or off-line).

All of these methods, however, face certain challenges. For the sake of accuracy, each mixture to be measured requires the empirical determination of the relationship between the mixture's concentration and density. When many mixtures are involved, this can result in a great deal of upfront effort. To minimize this upfront effort, one of two models relating a mixture's concentration to its density is commonly used.

NON-LINEAR MODEL (Insoluble, Two-component System):

Modeling the case of a mixture (M) where the solute (S) is completely insoluble in the solvent (L), the volumes (V) are additive:

$$V_M = V_S + V_L \qquad \text{Eq.1}$$

Therefore:

$$\frac{m_M}{\rho_M} = \frac{m_M \cdot x_S}{\rho_S} + \frac{m_M \cdot (1 - x_S)}{\rho_L} \qquad \text{Eq. 2-1}$$

where: m=mass, and, $\rho$= density; or, $$\frac{1}{\rho_M} = \frac{x_S}{\rho_S} + \frac{1 - x_S}{\rho_L} \qquad \text{Eq. 2-2}$$

Solving Eq. 2-2 for the mixture's solute content, $x_S$:

$$x_S = \frac{\rho_S(\rho_M - \rho_L)}{\rho_M(\rho_S - \rho_L)} \qquad \text{Eq. 3}$$

Eq.3 can be rewritten as:

$$x_S = \frac{\rho_S}{(\rho_S - \rho_L)} - \frac{\rho_S \cdot \rho_L}{(\rho_S - \rho_L)}\left(\frac{1}{\rho_M}\right) \qquad \text{Eq. 4}$$

Therefore, on a plot comparing the mixture's concentration to the inverse of it's density:

$$\text{Slope} = \frac{\rho_S \cdot \rho_L}{(\rho_S - \rho_L)}; \quad y\text{-Intercept} = \frac{\rho_S}{(\rho_S - \rho_L)}$$

LINEAR MODEL (Soluble, Two-component System):

Modeling the case of a mixture (M) where the solute is considered soluble in the solvent, it is assumed that the density of the mixture varies linearly from the density of the pure solvent (L) to the density of the pure solute (S), based on the mass ratio of the two components.

This model is expressed as:

$$x_S = \frac{\rho_M - \rho_L}{\rho_S - \rho_L} \qquad \text{Eq. 5-1}$$

which can be re-written as:

$$x_S = -\frac{\rho_S}{\rho_S - \rho_L} + \frac{\rho_M}{\rho_S - \rho_L} \qquad \text{Eq. 5-2}$$

Therefore, on a plot comparing the mixture's solids content to the it's density:

$$\text{Slope} = \frac{1}{\rho_S - \rho_L}; \quad y\text{-Intercept} = -\frac{\rho_L}{\rho_S - \rho_L}$$

In both of the above, the formula components are defined as follows:

$V_M$=Total System Volume (Volume of Mixture)
$V_S$=Volume of the Solute
$V_L$=Volume of the Solvent
$m_M$=Total System Mass (Mass of Mixture)
$x_S$=Mass Fraction of the Solute
$x_L$=Mass Fraction of the Solvent
$\rho_M$=Density of Mixture
$\rho_S$=Absolute Density (not Bulk Density) of Solute
$\rho_L$=Density of Solvent However, both of these common models used make erroneous assumptions. In the Non-Linear Model, it is assumed that the volumes of the components are completely additive, meaning that the components are completely insoluble in each other. This is very rarely the case. Most real world cases employ a solution of soluble or partially soluble solutes. In these cases, this model tends to overestimate the solution's concentration. In the Linear Model, the assumption fails because it does not compensate for the molecular interactions between the solute and the solvent. In either case, the assumptions often introduce enough error to render the results useless, as shown in Table 1.

manufacturers in effectively monitoring and operating their processes. Specifically, this data can be used, based on the manufacturing process, to do such things as:

1) control a known process fluid to a targeted concentration, e.g. in a paper coating process,
2) verify on-line the accuracy of batchwise or continuous ratio blends such as food products (ketchup, mayonnaise, syrup), personal care products (skin cream, shampoo), paints, petroleum blends, etc., and
3) eliminate excessive empirical work necessary with density monitoring process control systems.

The present invention is an improvement in that it more accurately converts a measured mixture density ($\rho M$) to concentration (m) through the formula:

$$m = \frac{1}{\left(1 - \rho_L \sum_{i=1}^{n} \frac{k_i x_i}{(\rho_S)_i}\right)} - \frac{\rho_L}{\left(1 - \rho_L \sum_{i=1}^{n} \frac{k_i x_i}{(\rho_S)_i}\right)} \left(\frac{1}{\rho_M}\right)$$

wherein $\rho L$ is the (temperature-dependent) density of the solvent, $k_i$ is the Additive Volume Coefficient for each solute, $x_i$ is the weight-% dry for each solute, $(\rho_S)_i$ is the (temperature-dependent) density of each solute, and $\rho M$ is the (temperature-dependent) density of the mixture.

Advantages of the present invention will become more apparent from the detailed description given hereinafter. However, it should be understood that the detailed description and specific Examples are given by way of illustration

TABLE 1

Examples of Model Inaccuracies.

| SOLUTION | CONC. | NON-LINEAR MODEL CONCENTRATION | NON-LINEAR MODEL % ERROR | LINEAR MODEL CONCENTRATION | LINEAR MODEL % ERROR |
| --- | --- | --- | --- | --- | --- |
| sodium chloride | 26.0% | 30.3% | 16.4% | 16.7% | 35.7% |
| barium chloride | 26.0% | 29.5% | 13.4% | 9.8% | 62.4% |
| magnesium sulfate | 26.0% | 36.6% | 40.8% | 17.8% | 31.4% |
| ferric sulfate | 40.0% | 45.7% | 14.4% | 21.4% | 46.5% |
| calcium chloride | 40.0% | 62.5% | 56.2% | 47.6% | 19.1% |
| sodium thiosulfate | 40.0% | 69.2% | 72.9% | 57.4% | 43.4% |
| ferric chloride | 50.0% | 55.9% | 11.7% | 31.1% | 37.8% |
| potassium carbonate | 50.0% | 62.3% | 24.6% | 41.9% | 16.2% |
| sodium hydroxide | 50.0% | 64.9% | 29.8% | 46.5% | 7.0% |

SUMMARY OF THE INVENTION

The present invention provides a new method for predicting the concentration of a solid/liquid or liquid/liquid mixture by use of the mixture's true density. This method makes use of a model, referred to herein as the Concentration-Density Model, which is an improvement over current methods of relating a mixture's concentration and density. This model introduces a novel concept referred to as the Additive Volume Coefficient (AVC), which reflects the change in volume that occurs after dissolving or mixing a solute into a solvent. The AVC is an important concept and provides this method with advantages over current technology.

The present invention provides a more accurate measurement of concentration than current technologies, and applies to a wider range of applications. As a result, the present invention, when coupled with an on-line measurement of solution density, provides accurate, continuous, real time feedback of a process fluid's concentration. This measurement is valuable to various industries in that it can assist only. Various changes and modifications within the spirit and scope of the invention will become apparent to those skilled in the art from this detailed description.

BRIEF DESCRIPTION OF THE DRAWINGS

The present invention will be more fully understood from the detailed description given hereinbelow and from the accompanying drawings. These drawings are provided by way of illustration only, and thus do not in any way limit the present invention.

DETAILED DESCRIPTION OF THE INVENTION

The present invention provides a new method for predicting the concentration of a solid/liquid or liquid/liquid mixture by use of the mixture's true density. This method provides a more accurate concentration measurement to a wider range of applications than any one current method or technology. It consists of theoretically determining the linear relationship between a mixture's concentration and density with the aid of a model referred to herein as the Concentration-Density Model.

The Concentration-Density Model is founded on the basic and straightforward principle that the volume of a mixture (slurry or solution) is different from the combined original volumes of the mixture's components if any level of solvency exists between these components. This Model incorporates the novel concept referred to herein as the Additive Volume Coefficient (AVC), which quantifies the change in volume that occurs after dissolving or mixing a solute into a solvent. As will be seen below, this Model uses a measurement of the mixture's density and the composition of the solutes in the mixture to calculate the mixture's concentration. For ease of practice, it is assumed that an accurate measurement of mixture density is provided.

Concentration-Density Model Factors:

$k_i$=Additive Volume Coefficient for $i^{th}$ solute component. $f$(conc., temp.)

$x_i$=Solute mass fraction of total solute mixture.

$(\rho_S)_i$=Density of it solute, which is temperature dependent.

$\rho_L$=Density of solvent, which is temperature dependent.

$\rho_M$=Density of mixture, which is temperature dependent.

m=Concentration (expressed as a fraction).

$V_M$=Volume of mixture.

$V_S$=Volume of solutes in mixture.

$V_L$=Volume of solvent in mixture.

$C_i$=Coefficient of Thermal Expansion for $i^{th}$ solute component.

$C_L$=Coefficient of Thermal Expansion for water.

$C_M$=Coefficient of Thermal Expansion for the mixture.

$\sum_{i=1}^{n} \Delta m_i$ = Concentration correction caused by density variation due to a temperature difference between the production temperature and the density reference temperature.

CONCENTRATION-DENSITY MODEL (Multicomponent Systems):

The basic principle of the model is simple and straightforward. The volume of a mixture (slurry or solution) is different than the original volumes of the mixture's components, if any level of solvency exists between these components. This can be expressed as:

$$V_M = V_S + V_L \qquad \text{Eq. 6}$$

For one unit of mixture mass, it can directly be obtained that the volumes of mixture and liquid are $$V_M = \frac{1}{\rho_M} \text{ and } V_L = \frac{(1-m)}{\rho_L},$$

respectively. As for solutes, their volume, when in the mixture, is expressed by:

$$V_S = \frac{k_1 x_1 m}{(\rho_S)_1} + \frac{k_2 x_2 m}{(\rho_S)_2} + \Lambda + \frac{k_n x_n m}{(\rho_S)_n} = m \sum_{i=1}^{n} \frac{k_i x_i}{(\rho_S)_i} \qquad \text{Eq. 7}$$

From Eq. 6 and Eq. 7 above, we have:

$$\frac{1}{\rho_M} = m \sum_{i=1}^{n} \frac{k_i x_i}{(\rho_S)_i} + \frac{1-m}{\rho_L} \qquad \text{Eq. 8}$$

By solving Eq. 8 above, the concentration in the mixture can be derived as:

$$m = \frac{\rho_M - \rho_L}{\rho_M \left(1 - \rho_L \sum_{i=1}^{n} \frac{k_i x_i}{(\rho_S)_i}\right)} \qquad \text{Eq. 9}$$

Eq. 9, above, can be rewritten as:

$$m = \frac{1}{\left(1 - \rho_L \sum_{i=1}^{n} \frac{k_i x_i}{(\rho_S)_i}\right)} - \frac{\rho_L}{\left(1 - \rho_L \sum_{i=1}^{n} \frac{k_i x_i}{(\rho_S)_i}\right)} \left(\frac{1}{\rho_M}\right) \qquad \text{Eq. 10}$$

where: $\text{Slope} = \frac{1}{\left(1 - \rho_L \sum_{i=1}^{n} \frac{k_i x_i}{(\rho_S)_i}\right)}$ and $\text{y - Intercept} = \frac{\rho_L}{\left(1 - \rho_L \sum_{i=1}^{n} \frac{k_i x_i}{(\rho_S)_i}\right)}$ Eq. 10, above, indicates that concentration is linearly proportional to the inverse of the mixture density. This relationship has a slope and y-intercept which is dependent on the Additive Volume Coefficient (AVC), the composition of the solutes, and the density of all mixture components.

Since the AVC is a function of concentration and temperature, and density is a function of temperature, compensations may be made to Eq. 10, if necessary, for changes in concentration or temperature. This would be done by differentiating Eq. 10 with respect to the variable(s) in question. For example, the effects of temperature on the density of the solution components can be compensated for by incorporating the relationship between density and temperature:

$$(\rho_i) = C_i (\Delta T) \qquad \text{Eq. 11}$$

By differentiating Eq.10 with respect to $\rho$ as a function of T, we can estimate it's influence on the mixture's concentration as:

$$\sum_{i=1}^{n} \Delta m_i = \qquad \text{Eq. 12}$$

$$-\frac{\rho_L \sum_{i=1}^{n} \frac{k_i x_i c_i}{(\rho_S)_i^2}}{\left(1 - \rho_L \sum_{i=1}^{n} \frac{k_i x_i}{(\rho_S)_i}\right)^2} (\Delta T) + \frac{(\rho_L)^2 \sum_{i=1}^{n} \frac{k_i x_i c_i}{(\rho_S)_i^2}}{\left(1 - \rho_L \sum_{i=1}^{n} \frac{k_i x_i}{(\rho_S)_i}\right)^2} \left(\frac{1}{\rho_M}\right)(\Delta T) +$$

-continued $$\frac{c_L \sum_{i=1}^{n} \frac{k_i x_i}{(\rho_S)_i}}{\left(1 - \rho_L \sum_{i=1}^{n} \frac{k_i x_i}{(\rho_S)_i}\right)^2}(\Delta T) - \frac{c_L}{\left(1 - \rho_L \sum_{i=1}^{n} \frac{k_i x_i}{(\rho_S)_i}\right)^2}\left(\frac{1}{\rho_M}\right)(\Delta T) + \qquad 5$$

$$\frac{\rho_L}{\left(1 - \rho_L \sum_{i=1}^{n} \frac{k_i x_i}{(\rho_S)_i}\right)^2}\left(\frac{c_M}{\rho_M^2}\right)(\Delta T)$$

Yet, even in it's most basic form (Eq. 10), ignoring the effects of concentration and temperature, this model requires inputs other than the measured density. These additional inputs consist of:

1) the density of the mixture's solvent,
2) the true density of each solute, liquid or solid, within the mixture,
3) the composition of the solute mixture, and,
4) the AVC for each solute within the mixture.

The density of the mixture components are constants, and are usually available from a variety of sources.

The composition of the solute mixture, on the other hand, requires some knowledge from manufacturing. In many manufacturing environments, the mixture being measured has been made internally, and therefore, the composition of each solute is known.

The AVC is introduced as a constant unique to a solute-solvent mixture at a constant concentration and temperature. As such, this AVC need only be determined once for each raw material in use. Over time, as AVC's are documented, obtaining these data would be no more difficult than obtaining component densities.

Figure 1:
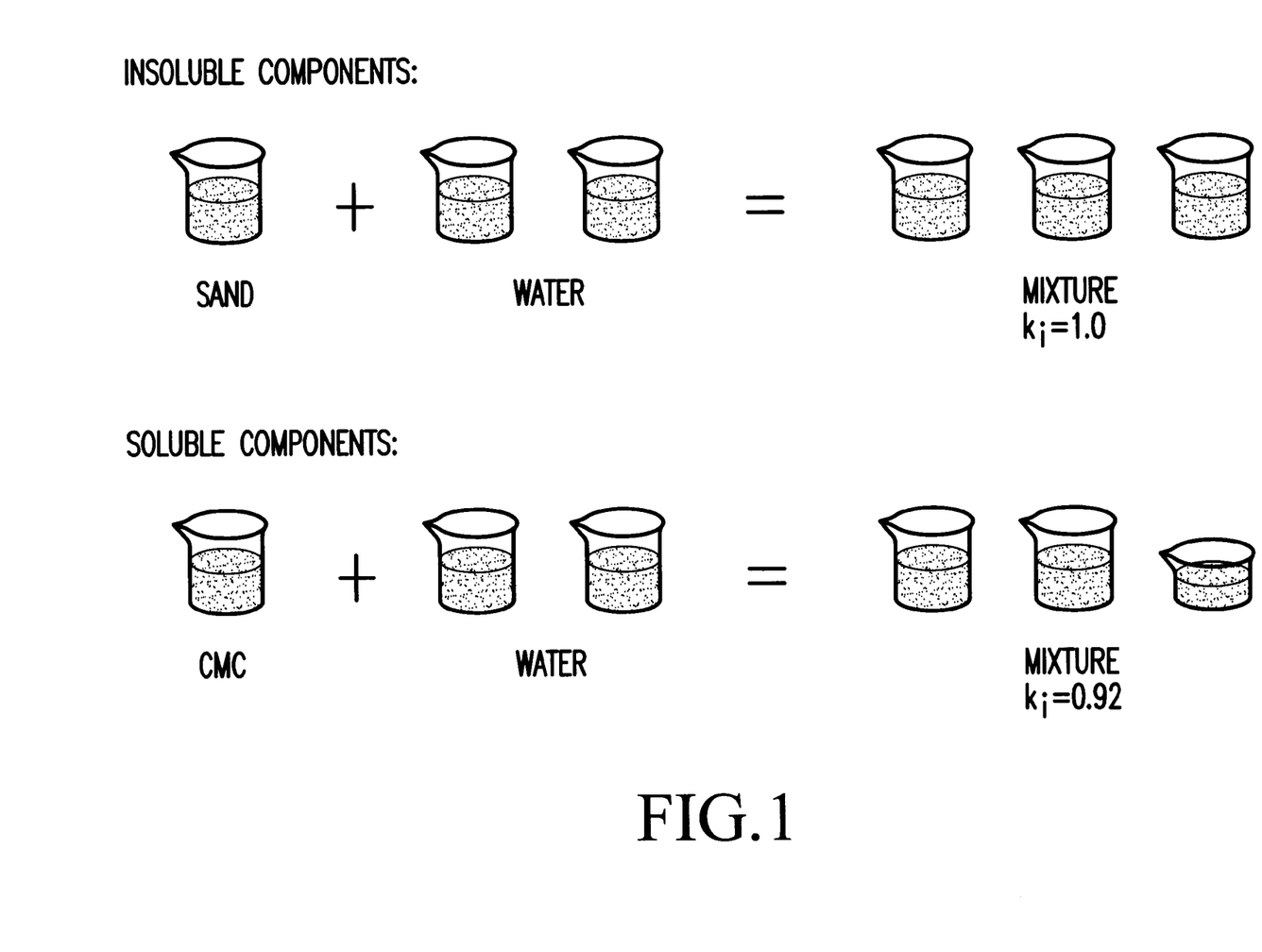
FIG. 1 graphically depicts the concept of the Additive Volume Coefficient.

FIG. 1 graphically illustrates the concept of the Additive Volume Coefficient. Completely insoluble components have volumes which are completely additive. The example shows 1 unit volume of sand and 2 unit volumes of water equaling 3 unit volumes of mixture. And partially or completely soluble components have volumes which are less than additive. Shown is an example of CarboxyMethylCellulose (CMC) and water. CMC is partially soluble in water. The example shows 1 unit volume of CMC in 2 unit volumes of water resulting in less than 3 unit volumes of mixture.

Specific examples can be found in Table 2.

$k$=Additive Volume Coefficient for a solute component. $f$(conc., temp.)

$m$=The concentration of the mixture, measured via a lab method.

$VT_b$=Total volume of the substance before mixing.

$VT_a$=Total volume of the substance after mixing.

$W_S$=Mass of solute.

$W_L$=Mass of solvent.

$\rho_S$=Density of solute. KNOWN $\rho_L$=Density of liquid (solvent). KNOWN $\rho_M$=Density of mixture.

$V_S$=Volume of solute to be mixed.

$V_L$=Volume of liquid (solvent) to be mixed.

METHOD of DETERMINING AVC
FOR A SINGLE-PHASE SOLUTE (Solid or Liquid):

Measure the mass of solvent ($W_L$).

Calculate the volume of solvent to be mixed:

$$V_L = \frac{W_L}{\rho_L} \qquad \text{Eq. 12}$$

Measure the mass of solute ($W_S$).

Calculate the volume of solute to be mixed:

$$V_S = \frac{W_S}{\rho_S} \qquad \text{Eq. 13}$$

Calculate the total volume of the substances before mixing ($VT_b$):

$$VT_b = V_L + V_S \qquad \text{Eq. 14}$$

Mix the solute and solvent.

Measure the density of the mixture to determine the total volume of the substances after mixing ($VT_a$):

$$VT_a = \frac{W_L + W_S}{\rho_M} \qquad \text{Eq. 15}$$

TABLE 2

Volume change and AVC examples.

| SOLUTE | SOLVENT | SOLUTE VOLUME | SOLVENT VOLUME | (NON-LINEAR MODEL) ADDED VOLUME | ACTUAL VOLUME | AVC |
|---|---|---|---|---|---|---|
| nickel sulfate | water | 1.1 | 96.0 | 97.1 | 95.9 | −0.110 |
| sodium hydroxide | water | 3.8 | 92.0 | 95.8 | 91.8 | −0.043 |
| magnesium sulfate | water | 9.8 | 74.0 | 83.8 | 77.0 | 0.309 |
| sodium thiosulfate | water | 24.0 | 60.0 | 84.0 | 72.2 | 0.509 |
| calcium chloride | water | 21.9 | 60.0 | 81.9 | 71.5 | 0.528 |
| potassium carbonate | water | 21.8 | 50.0 | 71.8 | 64.8 | 0.679 |
| sodium chloride | water | 12.0 | 74.0 | 86.0 | 83.5 | 0.791 |

This AVC, and a method for determining this AVC, is defined below for a two component system. This method can also be applied to multi-component systems.

Additive Volume Coefficient Factors:

Calculate the additive volume coefficient ($k$):

$$k = 1 - \frac{VT_b - VT_a}{V_S} \qquad \text{Eq. 16}$$

METHOD of DETERMINING AVC FOR A DUAL-PHASE SOLUTE (Solute in a Slurry Form):

Measure the concentration of the slurry (m).

Calculate the volumes of solvent ($V_L$) and solute ($V_S$), based on one unit mass of slurry:

$$V_L = \frac{1-m}{\rho_L} \qquad \text{Eq. 17}$$

and $$V_S = \frac{m}{\rho_S} \qquad \text{Eq. 18}$$

Determine the total volumes of the substances before ($VT_b$) and after ($VT_a$) mixing via:

$$VT_b = \frac{1-m}{\rho_L} + \frac{m}{\rho_S} \qquad \text{Eq. 19}$$

and $$VT_a = \frac{1}{\rho_M} \qquad \text{Eq. 20}$$

Calculate the additive volume coefficient (k) as:

$$k = 1 - \frac{VT_b - VT_a}{V_S} \qquad \text{Eq. 21}$$

Neglecting the effects of temperature on AVC, a relationship between the AVC of a solute-solvent pair and the concentration of the solute-solvent mixture can be developed by determining the AVC of the mixture at multiple concentrations and using regression analysis. Advancing this study to also include the effects of temperature would develop a relationship expressing AVC as a function of temperature and concentration. However, within a production environment these variables (temperature, concentration) likely operate within a narrow range. Therefore, the AVC can likely be simplified to be dependent on one or none of these variables for a specific application.

EXAMPLES

Example 1

% Solids Control in Coating Substrates

One application of this invention is the on-line determination of the % solids of a coating slurry applied to a substrate such as a paper web. This coating % solids data is then used to more efficiently control the application of the coating slurry onto the paper web. This benefit is realized due to the fact that % solids is often the primary coating property affecting the quantity of coating being applied to the paper web. As the accuracy of the measurement of coating slurry % solids is improved, the control of the quantity of this coating slurry is also improved.

Specifically, given a production environment in which the following production information is available to an on-line control system:

1) the dry coating component ratio,
2) the relationship between the Additive Volume Coefficient of each coating component and the concentration of the component in the mixture,
3) an on-line measurement of the density of the coating slurry, and,
4) the true density of each coating solid or solute; the following calculations are to occur within the control system to determine the coating slurry % solids:
   A. Determine the Concentration-Density Relationship.
   B. Estimate the coating slurry % solids.
   C. Calculate the AVC for each component based on the estimated % solids.
   D. Use an iteration process (e.g. Newton's Method) to determine the actual % solids of the coating slurry. (In manufacturing environments where the AVC can be accurately reduced to a constant, the use of Newton's Method is not necessary. This significantly reduces the calculations involved.)

Broadly speaking, this application of the present invention provides a method of monitoring a continuous coating of a substrate with solids delivered in a slurry of water. A first step in the present application comprises setting a target solids weight-% for the slurry. That is, in order to practice the present invention, one must determine what the solids weight-% in the coating slurry should be in order to provide a coated substrate having the desired properties. Having determined that target solids weight-%, one proceeds to provide a continuous industrial coating line with appropriate volumes of water and with appropriate amounts of the solid or solids with which it is desired to coat the substrate.

Figure 2:
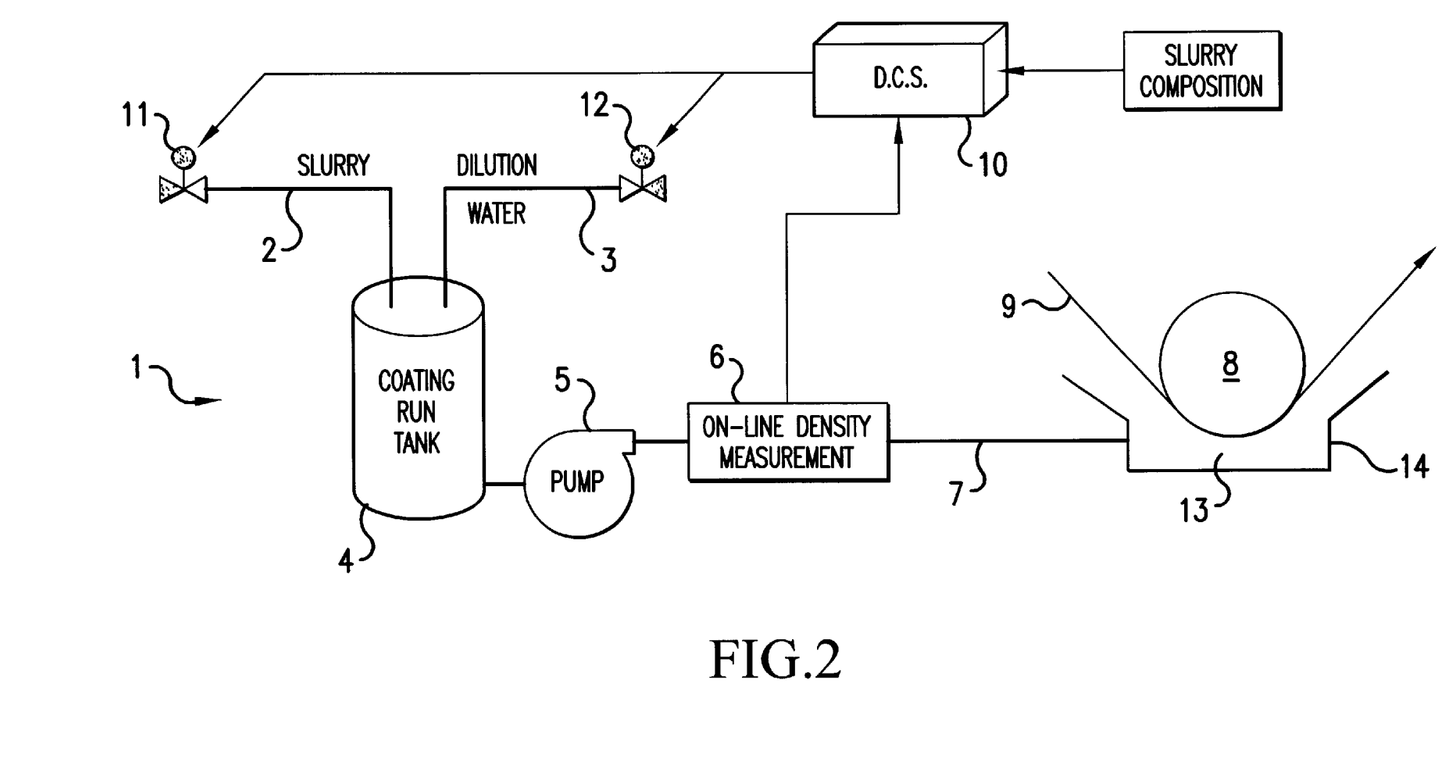
FIG. 2 is a schematic representation of an industrial coating line having an on-line measurement system in accordance with the present invention integrated into it.

In order to implement the present invention, one may modify a conventional industrial coating line by inserting an on-line density measurement system into it. Referring to FIG. 2, industrial coating line 1 comprises coating run tank 4, pump 5, and coating slurry bath 14. These elements are linked by piping 7. A roll 8 is partially immersed in bath 14, and substrate 9 travels around the roll through the bath where it contacts coating slurry 13. On-line density measurements 6, along with the composition of the coating slurry, are fed as inputs into distributed control system 10.

In accordance with the present invention, the distributed control system 10 converts these inputs to the solids weight-% of the coating. This, in turn, is compared to the target coating solids weight-% for the slurry. If there is a difference, the distributed control system 10 adjusts coating inflows 2 and 3 with flow control valves 11 and 12 as appropriate to correct this difference.

This Example represents use in one particular coating process. However, those skilled in the art will realize that this invention can be applied similarly to virtually any current coating method.

Example 2

Minimized Empirical Efforts in Controlling Syrup Makedown

Another application of this invention is the on-line determination of the concentration of sugars dissolved in water, commonly referred to as °Brix. This measurement is used to control the process of making syrup such as that used with canned fruit. Such a control provides the food manufacturer with the ability to control the product's sugar content. This provides the customer with a consistent taste over time, and/or the knowledge of a sugar content maximum, which is important to those with certain health conditions.

Current methods of measuring °Brix involve converting the measurement of syrup density to °Brix. This can be done using long-standing conversion tables available in the public domain. When incorporated into a control system, these conversions can occur on-line, thus providing real-time °Brix measurement. However, these conversion tables were developed using a sugar solution which was likely different than that being processed. This introduces a certain amount of error during the conversion of density to °Brix.

To overcome this error, manufacturers can re-develop this conversion relationship for their specific products. However, this process can be very time-consuming. When many such relationships must be developed, the time requirements involved may be prohibitive.

When used in conjunction with an on-line control system as described in Example 1, this invention eliminates the time-consuming need for manually developing these conversion relationships while providing a method for accurately converting density to °Brix.

The first step in this application comprises setting a target °Brix for the dilute syrup. Next, the flows of concentrated syrup and dilution water are controlled to maintain the dilute syrup at the targeted °Brix.

Figure 3:
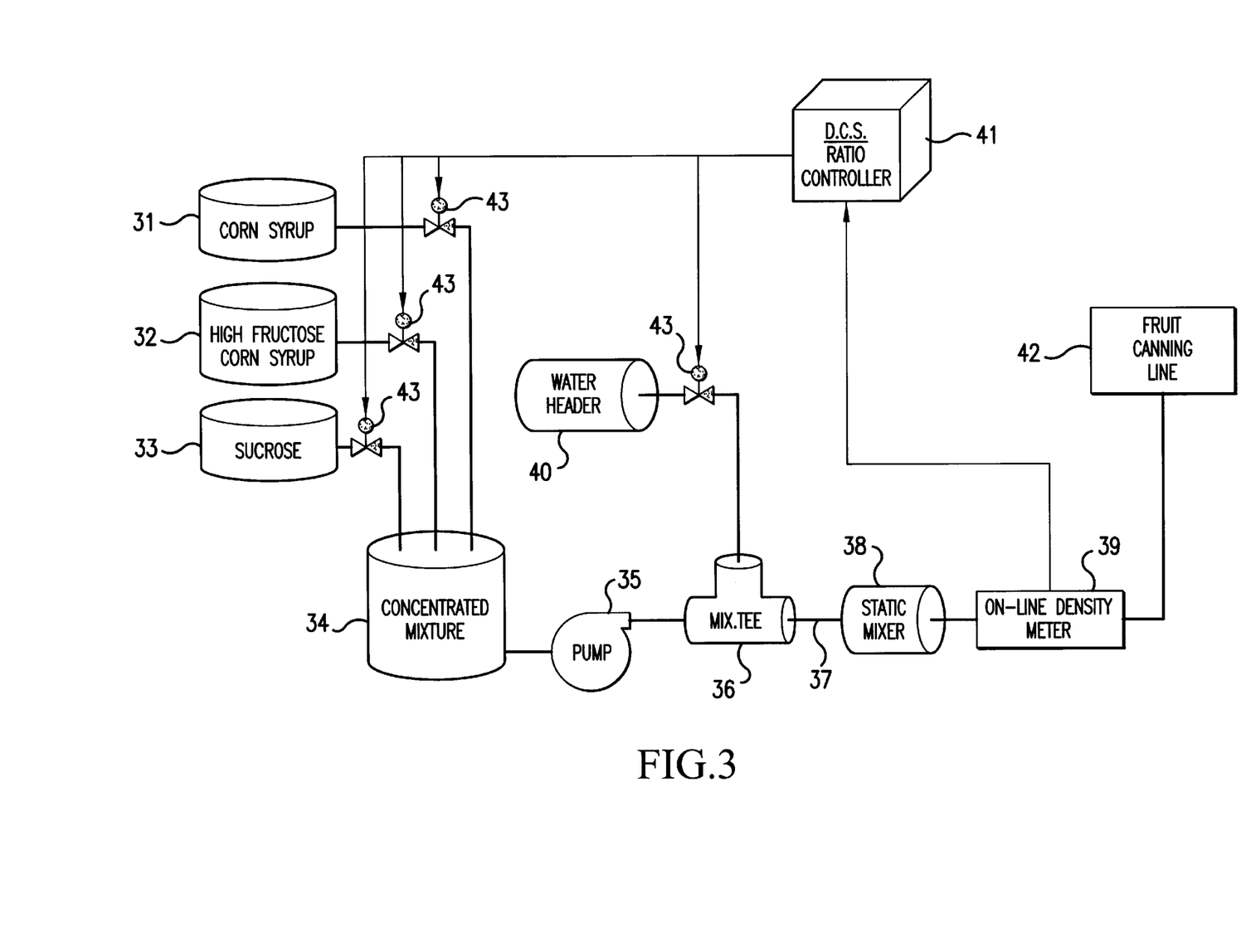
FIG. 3 is a schematic representation of a fruit canning line having a Distributed Control System operating in accordance with this invention.

Referring to FIG. 3, concentrated syrups 31, 32, and 33 are blended together as a concentrated mixture 4 in a ratio controlled by flow valves 43. The concentrated mixture travels through pump 35 to mixing tee 36 where it is blended with water from supply header 40. This dilute mixture travels through static mixer 38 to an on-line density meter 39.

The distributed control system 41 then converts the inputs to °Brix in accordance with the present invention. This, in turn, is compared to the target °Brix. If a difference exists, the distributed control system adjusts the flow control valves 33 and 34 to correct the discrepancy.

The invention being thus described, it will be evident that the same may be varied in many ways. Such variations are not to be regarded as a departure from the spirit and scope of the invention, and all such modifications as would be apparent to one skilled in the art likewise constitute a part of the present invention.

What is claimed is:

1. A method for automatically controlling the output of a continuous process that requires mixing of a solid or liquid component with a liquid carrier component (closed-loop control), which comprises:
   a.) setting a quantitative target for weight-% of one or more solids and/or concentration of one or more liquids to the liquid carrier component;
   b.) continuously mixing said solids and/or liquids with the liquid carrier component;
   c.) measuring the density of the mixture;
   d.) calculating the weight-% of solids and/or the liquid concentration in the mixture with the equation $$m = \frac{1}{\left(1 - \rho_L \sum_{i=1}^{n} \frac{k_i x_i}{(\rho_S)_i}\right)} - \frac{\rho_L}{\left(1 - \rho_L \sum_{i=1}^{n} \frac{k_i x_i}{(\rho_S)_i}\right)}\left(\frac{1}{\rho_M}\right)$$

wherein $\rho_L$ is the density of the liquid carrier component, $k_i$ is the Additive Volume Coefficient (AVC) for each solid or liquid, $x_i$ is the weight-% dry for each solid or the concentration for each liquid, $(\rho_S)_i$ is the density of each solid or liquid, and $\rho_M$ is the density of the mixture;
   e.) comparing the calculated weight-% solids or concentration to the target weight-% solids or concentration; and, if the calculated weight-% or concentration is greater or less than the target weight-% or concentration,
   f.) lowering or raising the amount of solids or liquids mixed in step b.).

2. A method for manually controlling the output of a continuous process that requires mixing of a solid or liquid component with a liquid carrier component (open-loop control), which comprises:
   a.) measuring the density of the mixture;
   b.) calculating the weight-% of solids and/or the liquid concentration in the mixture with the equation $$m = \frac{1}{\left(1 - \rho_L \sum_{i=1}^{n} \frac{k_i x_i}{(\rho_S)_i}\right)} - \frac{\rho_L}{\left(1 - \rho_L \sum_{i=1}^{n} \frac{k_i x_i}{(\rho_S)_i}\right)}\left(\frac{1}{\rho_M}\right)$$

wherein $\rho_L$ is the density of the liquid carrier component, $k_i$ is the Additive Volume Coefficient (AVC) for each solid or liquid, $x_i$ is the weight-% dry for each solid or the concentration for each liquid, $(\rho_S)_i$ is the density of each solid or liquid, and $\rho_M$ is the density of the mixture, and;
   c.) employing this mixture concentration result to make a decision regarding the present state of operations with respect to the concentration of the mixture.

3. A method for controlling the output of a continuous coating process which comprises:
   a.) setting a quantitative target for weight-% of one or more solids to be coated onto a substrate;
   b.) continuously applying the solids to the substrate via a carrier fluid;
   c.) measuring the density of the slurry;
   d.) calculating the weight-% of solids in the slurry with the equation $$m = \frac{1}{\left(1 - \rho_L \sum_{i=1}^{n} \frac{k_i x_i}{(\rho_S)_i}\right)} - \frac{\rho_L}{\left(1 - \rho_L \sum_{i=1}^{n} \frac{k_i x_i}{(\rho_S)_i}\right)}\left(\frac{1}{\rho_M}\right)$$

wherein $\rho_L$ is the density of the solvent, $k_i$ is the Additive Volume Coefficient for each solid, $x_i$ is the weight-% dry for each solid, $(\rho_S)_i$ is the density of each solid, and $\rho_M$ is the density of the slurry;
   e.) comparing the calculated weight-% solids to the target weight-% solids; and, if the calculated weight-% is greater or less than the target weight-%,
   f.) lowering or raising the amount of solids applied in step b.).

4. The method of claim 3, in which the substrate is a paper web and the solids component comprises clay.

5. A method for controlling the output of a continuous process for preparing a syrup which comprises:
   a.) setting a quantitative target for a concentration of one or more carbohydrates and/or carbohydrate-containing liquids to be blended into a syrup;
   b.) continuously supplying the carbohydrate and/or carbohydrate-containing liquid and a dilution liquid to a vessel and mixing said liquids to form a slurry;
   c.) measuring the density of the slurry;
   d.) calculating the carbohydrate concentration in the slurry with the equation $$m = \frac{1}{\left(1 - \rho_L \sum_{i=1}^{n} \frac{k_i x_i}{(\rho_S)_i}\right)} - \frac{\rho_L}{\left(1 - \rho_L \sum_{i=1}^{n} \frac{k_i x_i}{(\rho_S)_i}\right)} \left(\frac{1}{\rho_M}\right)$$

wherein $\rho_L$ is the density of the solvent, $k_i$ is the Additive Volume Coefficient for each solid, $X_i$ is the weight-% dry for each solid, $(\rho_S)_i$ is the density of each solid, and $\rho_M$ is the density of the slurry;

e.) comparing the calculated carbohydrate concentration to the target carbohydrate concentration; and, if the calculated carbohydrate concentration is greater or less than the target carbohydrate concentration, f.) lowering or raising the amount of carbohydrates and/or volume of carbohydrate-containing liquids supplied in step b.).

6. The method of claim 5, in which carbohydrates comprising sucrose and carbohydrate-containing liquids comprising corn syrup and high fructose corn syrup are mixed with a dilution liquid comprising water.

7. A method for determining the concentration of a solid or liquid component in a liquid carrier component, which comprises:

a.) measuring the density of the mixture;

b.) calculating the weight-% of solids and/or the liquid concentration in the mixture with the equation $$m = \frac{1}{\left(1 - \rho_L \sum_{i=1}^{n} \frac{k_i x_i}{(\rho_S)_i}\right)} - \frac{\rho_L}{\left(1 - \rho_L \sum_{i=1}^{n} \frac{k_i x_i}{(\rho_S)_i}\right)} \left(\frac{1}{\rho_M}\right)$$

wherein $\rho_L$ is the density of the liquid carrier component, $k_i$ is the Additive Volume Coefficient (AVC) for each solid or liquid, $X_i$ is the weight-% dry for each solid or the concentration for each liquid, $(\rho_S)_i$ is the density of each solid or liquid, and $\rho_M$ is the density of the mixture.

8. A method of characterizing a component which comprises determining the change in volume experienced by that component when it is combined with a solvent, such that this relationship is expressed by the equation $$k = 1 - \frac{VT_b - VT_a}{V_S}$$

wherein k is the Additive Volume Coefficient (AVC), $VT_b$ is the total volume of solute and solvent before mixing, $VT_a$ is the total volume of solute and solvent after mixing, and $V_S$ is the volume of solute.

9. A method of identifying a sample of unknown constitution which comprises comparing its volume loss on dissolution with a collection of volume losses on dilution for a variety of compounds determined according to the method of claim 8.

10. The method of any one of claims 1 through 9, in which the AVC is determined for a single-phase solid or liquid solute by:

measuring the mass of solvent ($W_L$);

$$V_L = \frac{W_L}{\rho_L};$$

calculating the volume of solvent to be mixed using the equation
measuring the mass of solute ($W_S$);

$$V_S = \frac{W_S}{\rho_S};$$

calculating the volume of solute to be mixed using the equation
calculating the total volume of the substances before mixing ($VT_b$) using the
equation $VT_b = V_L + V_S$;
mixing the solute and solvent;
measuring the density of the mixture to determine the total volume of the $$VT_a = \frac{W_L + W_S}{\rho_M};$$

substances after mixing ($VT_a$) using the equation and
calculating the additive volume coefficient using the equation $$k = 1 - \frac{VT_b - VT_a}{V_S}.$$

11. The method of any one of claims 1 through 9, in which the AVC is determined for a dual-phase solute in slurry form by:

measuring the concentration of the slurry (m); calculating the volume of solvent ($V_L$) and solute ($V_S$), based on one unit mass of slurry, using the equations $$V_L = \frac{1-m}{\rho_L} \text{ and } V_S = \frac{m}{\rho_S};$$

determining the total volumes of the substances before ($VT_b$) and after ($VT_a$) mixing using the equations $$VT_b = \frac{1-m}{\rho_L} + \frac{m}{\rho_S} \text{ and } VT_a = \frac{1}{\rho_M};$$

and
calculating the additive volume coefficient using the equation $$k = 1 - \frac{VT_b - VT_a}{V_S}.$$

* * * * *